United States Patent [19]
Carmichael et al.

[11] Patent Number: 5,908,779
[45] Date of Patent: Jun. 1, 1999

[54] TARGETED RNA DEGRADATION USING NUCLEAR ANTISENSE RNA

[75] Inventors: Gordon G. Carmichael, West Hardford; David B. Batt, New Britain; Zhong Liu, New Haven, all of Conn.

[73] Assignee: University of Connecticut, Storrs, Conn.

[21] Appl. No.: 08/160,058

[22] Filed: Dec. 1, 1993

[51] Int. Cl.⁶ .............................. C12N 5/00; C12N 15/00; A16K 48/00
[52] U.S. Cl. ........................... 435/325; 435/320.1; 514/44
[58] Field of Search .......................... 514/44; 435/172.3, 435/91.1, 91.31, 91.32, 240.1, 320.1; 536/24.5

[56] References Cited

U.S. PATENT DOCUMENTS

| | | | |
|---|---|---|---|
| 5,190,931 | 3/1993 | Inouye | 435/91 |
| 5,208,149 | 5/1993 | Inouye | 435/91 |

FOREIGN PATENT DOCUMENTS

| | | | |
|---|---|---|---|
| 0634289 | 2/1993 | Australia | C12N 15/11 |
| 0329308 | 8/1989 | European Pat. Off. . | |
| 0421376 | 4/1991 | European Pat. Off. | C12N 9/00 |

OTHER PUBLICATIONS

M. Stinski: et al J. Virology ('85) 55(2) 431–41.
M. Gossen et al. PNAS ('92) 89:5547–51.
M. Schena et al. PNAS ('91) 88:10421–25.
A. Miller Nature, vol. 357, (Jun. 11, 1992) pp. 455–460.
J. van Brunt Bio/Technology, vol. 6 (Oct. 1988) pp. 1149–1154.
M. Boshart et al. Cell, vol. 41 (Jun. 1985) pp. 521–530.
E. Uhlmann et al. Chemical Reviews, vol. 90 #4 (Jun. 1990) p. 576.
M. Barinaga Science, vol. 262 (Dec. 3, 1993) pp. 1512–1514.
Z. Liv et al. PNAS, vol. 91 (May 1994) pp. 4258–4262.
R. Mulligan Science, vol. 260 (May 14, 1993) pp. 926–932.
N. Dillon Tibtech, vol. 11 (May 1993) pp. 167–173.
Murray, J.A.H. and Crockett, N., "Antisense Techniques: An Overview," In *Antisense RNA and DNA*, (Wiley–Liss, Inc.) pp. 1–49 (1992).
Steinecke, P. et al., "Expression of a Chimeric Ribozyme Gene Results in Endonucleolytic Cleavage of Target mRNA and a Concomitant Reduction of Gene Expression In Vivo," *The EMBO J.*, 11(4):1525–1530 (1992).
Eckner, R., et al., "Mature mRNA 3' End Formation Stimulates RNA Export From the Nucleus," *The EMBO J.*, 10(11):3513–3522 (1991).
Tosic, M. et al., "Post–Transcriptional Events are Responsible for Low Expression of Myelin Basic Protein in Myelin Deficient Mice: Role of Natural Antisense RNA," *The EMBO J.*, 9(2):401–406 (1990).
Izant, J.G. and Weintraub H., "Constitutive and Conditional Suppression of Exogenous and Endogenous Genes by Anti-Sense RNA," *Science*, 229:345–352 (1985).
Lengyel, P., "Double–Stranded RNA and Interferon Action," *Journal of Interferon Research*, 7:511–519 (1987).

Cornelissen, M., "Nuclear and Cytoplasmic Sites for Anti–Sense Control," *Nucleic Acids Research*, 17(18):7203–7209 (1989).
Krystal, G., "Regulation of Eukaryotic Gene Expression by Naturally Occurring Antisense RNA," in *Gene Regulation: Biology of Antisense RNA and DNA* (Raven Press, Ltd.), pp. 11–20 (1992).
Kimelman, D., "Regulation of Eukaryotic Gene Expression by Natural Antisense Transcripts: The Case of the Modifying Reaction," in *Gene Regulation: Biology of Antisense RNA and DNA*, (Raven Press, Ltd.), pp. 1–9 (1992).
Lazar et al., "Gene Expression from the c–erbAα/Rev–ErbAα Genomic Locus," *The Journal of Biological Chemistry*, 265 (22):12859–12863 (1990).
Taira, K. et al., "Construction of a Novel Artificial–Ribozyme–Releasing Plasmid," *Protein Engineering*, 3(8):733–737 (1990).
Acheson, N.H., "Kinetics and Efficiency of Polyadenylation of Late Polyomavirus Nuclear RNA: Generation of Oligomeric Polyadenylated RNAs and Their Processing into mRNA," *Mol. and Cell. Biol.*, 4(4):722–729 (1984).
Weerasinghe, M. et al., "Resistance to Human Immunodeficiency Virus Type 1 (HIV–1) Infection in Human CD4⁺ Lymphocyte–Derived Cell Lines Conferred by Using Retroviral Vectors Expressing an HIV–1 RNA–Specific Ribozyme," *J. of Virology*, 65(10):5531–5534 (1991).
Dzianott, A.M. and Bujarski, J.J., "Derivation of an Infectious Viral RNA by Autolytic Cleavage of In Vitro Transcribed Viral cDNAs," *Proc. Natl. Acad. Sci. USA*, 86:4823–4827 (1989).
Cotten, M. and Birnstiel, M., "Ribozyme Mediated Destruction of RNA In Vivo," *The EMBO J.*, 8(12):3861–3866 (1989).
Taira, K. and Nishikawa, S., "Construction of Novel RNA–Transcript–Trimming Plasmids That Can be Used Both In Vitro in Place of Run–Off Transcriptions and In Vivo as Multi–Ribozymes Transcription Vectors," In *Raven Press Series on Molecular and Cellular Biology*, vol. 1, Erickson and Izant, Eds (Raven Press, Ltd., New York) pp. 35–54 (1992).

(List continued on next page.)

*Primary Examiner*—Bruce R. Campbell
*Attorney, Agent, or Firm*—Hamilton, Brook, Smith & Reynolds, P.C.

[57] ABSTRACT

The invention pertains to a novel method and construct for regulating gene expression through inhibition of gene expression by nuclear antisense RNA. The construct provides an efficient means for introducing, expressing and accumulating the antisense RNA in the nucleus. The antisense RNA hybridizes to the sense mRNA in the nucleus, thereby preventing both processing and cytoplasmic transport. The construct comprises a promoter, antisense sequences, and a cis- or trans-ribozyme which generates 3'-ends independently of the polyadenylation machinery and thereby inhibits the transport of the RNA molecule to the cytoplasm. The construct may also comprise a histone stem-loop structure that assists in stabilizing the transcripts against exonucleolytic degradation.

13 Claims, 5 Drawing Sheets

OTHER PUBLICATIONS

Liu, Z. et al., "Targeted Nuclear Antisense RNA Mimics Natural Antisense–Induced Degradation of Polyoma Virus Early RNA:" *Proc. Natl. Acad. Sci. USA*, 91:4258–4262 (1994).

Liu, Z. and Carmichael, G.G., "Nuclear Antisense RNA: An Efficient New Method to Inhibit Gene Expression," *Molelcular Biotechnology*, 2(2):107–119 (1994).

Kim et al. Cell, vol. 42 (Aug. 1985) pp. 129–138.

B. Cullen Cell, vol. 46 (Sep. 26, 1986) pp. 973–982.

J. Haseloff et al. Nature, vol. 334 (Aug. 18, 1988) pp. 585–591.

K. Culver et al., TIG, 10(5) (May 1994) 174–178.

A. Coghlam, New Scientist, (Nov. 25, 1995) pp. 14–15.

D. Brown, Washington Post, Friday, Dec. 8, 1995 A1, A22.

SEQUENCE LISTING (1) GENERAL INFORMATION:
  (i) APPLICANT: Carmichael, Gordon G. Batt, David B. Liu, Zhong
  (ii) TITLE OF INVENTION: Targeted RNA Degradation Using Nuclear Antisense RNA
  (iii) NUMBER OF SEQUENCES: 1
  (iv) CORRESPONDENCE ADDRESS:
    (A) ADDRESSEE: Hamilton, Brook, Smith & Reynolds, P. C.
    (B) STREET: Two Militia Drive
    (C) CITY: Lexington
    (D) STATE: Massachusetts
    (E) COUNTRY: US
    (F) ZIP: 02173-4799
  (v) COMPUTER READABLE FORM:
    (A) MEDIUM TYPE: Floppy disk
    (B) COMPUTER: IBM PC Compatible
    (C) OPERATING SYSTEM: PC-DOS/MS-DOS
    (D) SOFTWARE: PatentIn Release #1.0, Version #1.25
  (vi) CURRENT APPLICATION DATA:
    (A) APPLICATION NUMBER: US
    (B) FILING DATE:
    (C) CLASSIFICATION:
  (viii) ATTORNEY/AGENT INFORMATION:
    (A) NAME: Carroll Esq., Alice O.
    (B) REGISTRATION NUMBER: 33,542
    (C) REFERENCE/DOCKET NUMBER: UCT93-03
  (ix) TELECOMMUNICATION INFORMATION:
    (A) TELEPHONE: (617) 861-6240
    (B) TELEFAX: (617) 861-9540
(2) INFORMATION FOR SEQ ID NO:1:
  (i) SEQUENCE CHARACTERISTICS:
    (A) LENGTH: 103 base pairs
    (B) TYPE: nucleic acid
    (C) STRANDEDNESS: single
    (D) TOPOLOGY: linear
  (ii) MOLECULE TYPE: mRNA
  (xi) SEQUENCE DESCRIPTION: SEQ ID NO:1:
GGAUCCCCG AAUUAAUUCG GCCCUUAUCA GGGCCAUGCA UGUCGCGGCC GCCUCCGCGG 60
CCGCCUGAUG AGUCCGUGAG GACGAAACAU GCAUAUCAAG CUU 103

TARGETED RNA DEGRADATION USING NUCLEAR ANTISENSE RNA

GOVERNMENT SUPPORT

This work was supported by grant CA45382 from the National Cancer Institute. The Government has certain rights in the invention.

BACKGROUND OF THE INVENTION

The polyoma virus genome is a small circular double-stranded DNA molecule whose early and late transcription units proceed in opposite directions from an intergenic regulatory region. In the early phase of a productive life cycle, the early genes (encoding the large, middle and small T antigens) are preferentially expressed. Before the initiation of viral DNA replication, few late-strand messages can be detected (Beard et al., *J. Virol.* 17:20–26 (1976)). Once the infection enters the late phase (after the onset of DNA replication), late gene expression increases rapidly while the relative level of early gene expression is dramatically reduced.

The observation that polyoma virus mutants with temperature sensitive large T antigens overexpress their early genes at the nonpermissive temperature has led to the proposal that the viral early genes are negatively regulated by their own products (Farmerie and Folk, *Proc. Natl. Acad. Sci. USA* 81:6919–6923 (1984)). This autoregulation was thought to result from large T antigen binding to high affinity binding sites in the viral intergenic region and thereby inhibiting initiation from the early promoter (Fenton and Basilico, *Virology* 121:384–392 (1982)). However, it has been shown using nuclear run-on assays that the relative transcriptional activities from the early and late promoters change little throughout infection (Hyde-DeRuyscher and Carmichael, *Proc. Natl. Acad. Sci. USA* 85:8993–8997 (1988)). Regulation of early gene expression after transcription initiation is also consistent with the data of Farmerie and Folk (Ibid.), who observed early gene repression by large T antigen even in constructs where this transcription was driven by a heterologous promoter. Taken together these results suggest that regulation of early gene expression is at a post-transcriptional level.

It has been shown that transcription termination of the late genes is inefficient during the late phase of infection (Hyde-DeRuyscher and Carmichael, Ibid.), allowing RNA polymerase II to continue around the circular viral genome multiple times. The resulting giant primary transcripts are eventually processed by RNA splicing and polyadenylation, but unprocessed giant transcripts accumulate to high levels in the nucleus (Acheson, *Mol. Cell. Biol.* 4:722–729 (1984)). Due to the circularity of the polyoma genome, giant late-strand transcripts contain sequences complementary to early-strand transcripts, serving as natural antisense RNA. These giant transcripts accumulate at the same time that early-strand RNAs become relatively less abundant.

There is a growing body of literature devoted to antisense technology; however, this work has related only to cytoplasmic antisense RNA. (Murray, J. A. H. and Crockett, N., "Antisense Techniques: An Overview, " in *Antisense RNA and DNA*, (Wiley-Liss, Inc.) pp. 1–49 (1992)). There has been no work to date aimed at producing antisense RNA accumulated in the nucleus.

SUMMARY OF THE INVENTION

This invention pertains to the regulation of gene expression by nuclear antisense RNA. It is shown herein that the naturally occurring polyoma antisense early RNA generated from the late transcription unit is almost exclusively present in the nucleus. Furthermore, it is shown herein that polyoma early-strand RNAs are reduced by expression and accumulation in the nucleus of antisense-early RNAs. It is demonstrated that antisense RNAs can be expressed and accumulated in the nucleus using a construct comprising a promoter, antisense sequences, and sequences encoding a cis-ribozyme and optionally a stem loop structure. The cis-ribozyme is incorporated into the antisense construct in order to generate 3'-ends independently of the polyadenylation machinery and thereby inhibit transport of the RNA molecule to the cytoplasm. The construct may optionally contain a histone stem loop structure to aid in stabilizing the transcripts against exonucleolytic degradation. This invention has application to several areas. It may be used as a therapeutic agent, targeting and inhibiting harmful native gene expression. It may also be used therapeutically to inhibit viral gene expression, thereby making cells resistant to and curing viral infection. This invention also has application as a research tool with the ability to inhibit expression of any targeted gene.

BRIEF DESCRIPTION OF THE DRAWINGS

FIG. 1 depicts the "late" transcription units of the polyoma mutants used in this study. Wild type (WT) encodes the late leader exon and two alternative splice sites, used for production of messages for the structural proteins VP3 and VP1. Mutant 5'ssΔ lacks 6 nucleotides (nt) (GTAAGT) at the 5' splice site bordering the late leader exon and expresses lower than wild type levels of antisense RNA to the viral early region (Barrett et al., *Nucleic Acids Res.* 19:3011–3017 (1991).

FIGS. 2A–2B show constructs expressing antisense early RNA in the nucleus. A. Antisense constructs used in this study. Construct αE-RZ contains the antisense polyoma early region driven by the cytomegalovirus (CMV) promoter, with 3' end formation the result of cleavage by a cis-ribozyme. Construct E-RZ contains the same polyoma early region and the ribozyme sequence but no CMV promoter or polyoma replication origin. Construct Py-CMV contains only the CMV promoter and polyoma replication origin. The orientation of the polyoma early region is indicated by the arrowheads. The RNA probe Ribo-Ava is also shown. B. Sequence of the ribozyme and the histone stem-loop structure used in the construction of the plasmids shown in panel A. The vertical arrow indicates the cleavage site of the cis-ribozyme. The optional histone stem-loop structure used to stabilize the transcripts against possible exonucleolytic degradation is indicated.

FIG. 3 illustrates subcellular distribution of antisense RNA transcripts produced by construct αE-RZ. This subcellular distribution was determined in cells cotransfected with construct αE-RZ (the antisense expression vector) and mutant 5'ssΔ (the target plasmid). Mutant 5'ssΔ was used because it overexpresses early RNA and allows αE-RZ replication. Virtually all antisense RNA produced from construct αE-RZ remains in the nucleus. It is also evident that ribozyme cleavage is incomplete, with only about 80% of the transcripts being cleaved. However, uncleaved transcripts also remain in the nucleus, as do the antisense-early transcripts from mutant 5'ssΔ.

DETAILED DESCRIPTION OF THE INVENTION

The present invention pertains to a novel method and construct for regulating gene expression through inhibition of gene expression by nuclear antisense RNA. The construct provides an efficient means for introducing, expressing and accumulating the antisense RNA in the nucleus. The antisense RNA hybridizes to the sense mRNA in the nucleus, thereby preventing both processing and cytoplasmic transport. The construct comprises a promoter, an origin of replication, antisense sequences, and a cis- or trans-ribozyme which generates 3'-ends independently of the polyadenylation machinery and thereby inhibits the transport of the RNA molecule to the cytoplasm. The construct may also comprise a histone stem-loop structure that assists in stabilizing the transcripts against exonucleolytic degradation.

The advantages of this invention over prior cytoplasmic antisense technology are three-fold. First, this invention closely mimics the system of naturally-occurring antisense regulation seen in a variety of organisms, indicating that it is a natural means for studying antisense regulation of gene expression. Also, this invention solves at least one problem created by cytoplasmic antisense RNA, namely the activation of interferon by double stranded RNAs. There is no indication that nuclear antisense RNA causes interferon activation, and therefore there is less risk of adverse effects on the cell. (Lengyel, P., *Journal of Interferon Research* 7:511–519 (1987)). Furthermore, the efficiency of nuclear antisense RNA far exceeds that of cytoplasmic RNA. While in cytoplasmic RNA experiments the ratio of antisense to sense transcripts required for inhibition is typically on the level of 100 or 1000 to 1, data from nuclear antisense experiments indicates that the same level of regulation can be achieved with an antisense to sense ratio of as little as 5 to 1. This enhanced effectiveness is of great advantage both from an efficiency and cost-effectiveness standpoint.

Once introduced into the cell nucleus, the construct begins expressing the antisense sequences following the promoter. The construct contains none of the usual transcription termination sequences (typically associated with polyadenylation signals); instead a cis- or trans-ribozyme (SEQ ID NO. 1) is inserted to cleave the transcript without normal polyadenylation. This variation prohibits transportation of the antisense sequences from the nucleus to the cytoplasm. As the antisense sequences accumulate in the nucleus, they hybridize to their complementary sense RNA transcripts. It is believed that the formation of these hybrids prevents processing and cytoplasmic transport of the RNA, as these hybrids are shown to remain in the nucleus and are eventually degraded. By hybridizing to a targeted gene, the antisense transcripts can regulate and inhibit expression of that gene. This function has utility in both therapeutic and research applications.

The promoter segment can be chosen from a wide range of constitutive or inducible promoters. Of particular interest but not exclusive are the constitutive promoters of the human cytomegalovirus (CMV) and Rous sarcoma virus (RSV), as well as the Simian virus 40 and Herpes simplex promoters. Useful inducible promoters include antibiotic resistant promoters, heat-shock promoters, the hormone-inducible mammary tumor promoter and the metallotheionein promoter.

The ribozyme component is included for the purpose of producing the 3' end independent of the cellular polyadenylation machinery. A cis-ribozyme with the ability to generate 3' ends in this manner is expected to achieve the desired result; however, of particular interest are the hammerhead cis-ribozyme (described in the Examples) and the human hepatitis delta virus ribozyme, which is believed to cleave transcripts faster and more efficiently than the hammerhead ribozyme. Trans-ribozymes can be used as an alternative.

This invention has application to the regulation of genes, and therefore the antisense sequences of interest are numerous. However, the sequence of the target gene should be known before its complementary antisense can be created. Thus, antisense sequences can be utilized based on the sequence of the gene desired for targeting.

The construct of this invention may optionally contain histone stem-loop structure for the purpose of stabilizing the cleaved antisense transcript against exonucleolytic degradation. However, depending on the desired duration of the result, this component may be omitted. In fact, published evidence (Eckner et al.) suggests that this structure stabilizes RNAs only in the cytoplasm.

Figure 2A:
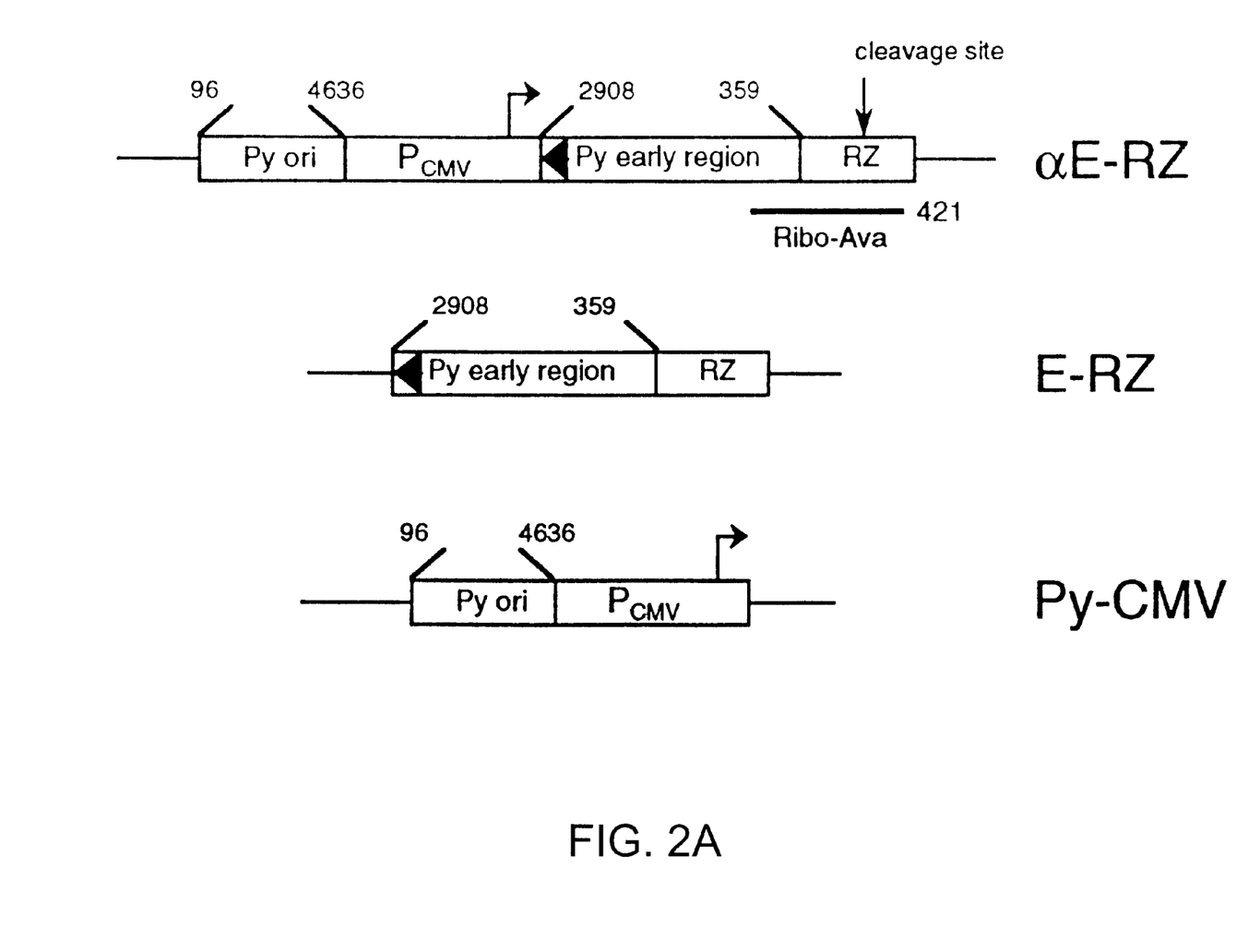
Figure 2B:
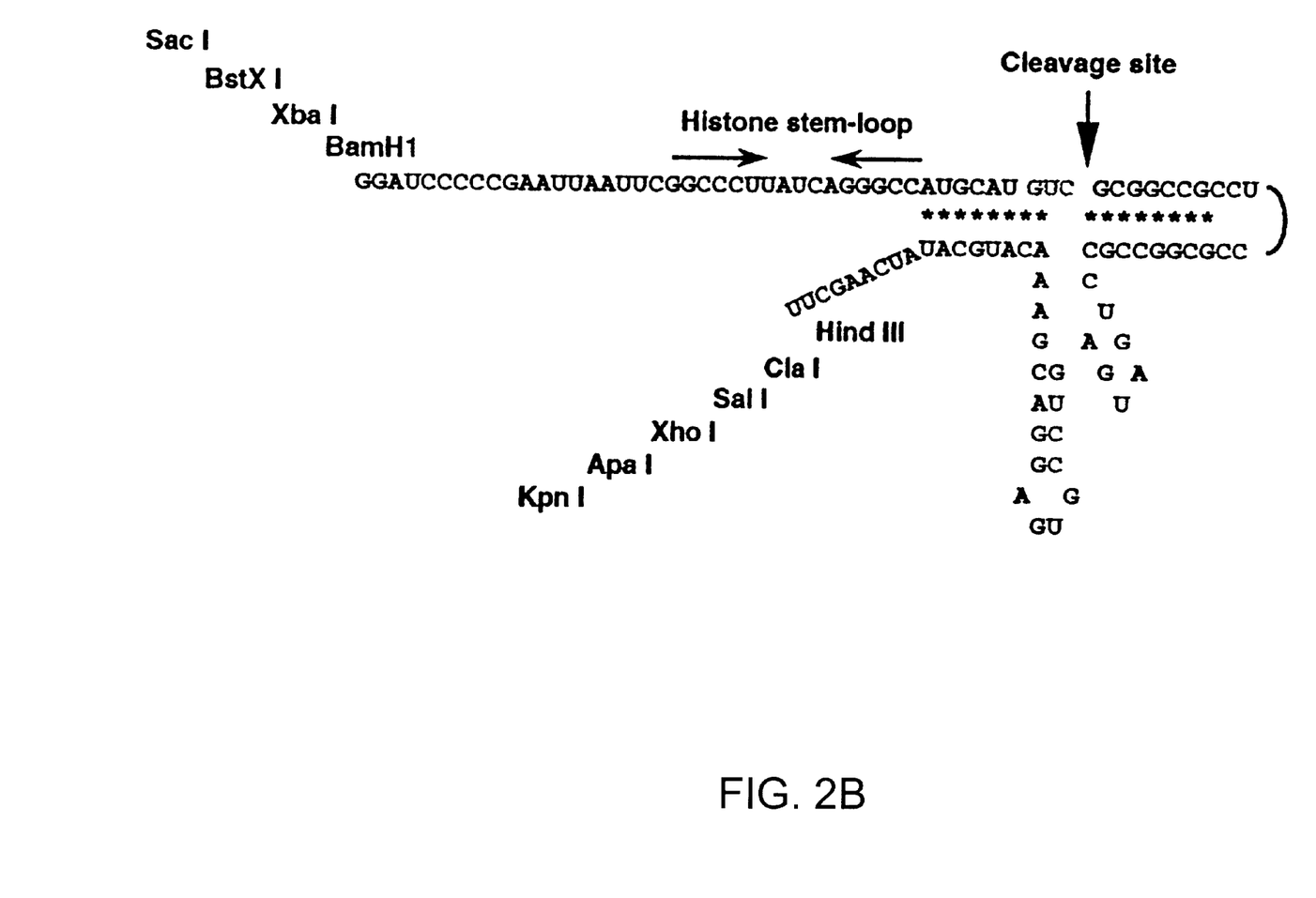

In a preferred embodiment, regulation of target gene expression is achieved using a novel DNA construct shown in FIG. 2A. This construct, αE-RZ, contains sequences encoding a self-cleaving ribozyme (FIG. 2B), flanked by a number of unique restriction enzyme cleavage sites, to facilitate cloning into other constructs. Immediately upstream of the ribozyme is a histone stem-loop structure to possibly retard degradation. The ribozyme cassette is inserted into standard cloning vector pBlueScript SKII. This ribozyme cassette is then excised and inserted into construct αE-RZ (FIG. 2A). This preferred embodiment incorporates a functional polyoma virus replication origin (nt 4636-96) to allow replication and amplification in mouse cells in the presence of large T antigen. Construct αE-RZ also contains a promoter derived from the human cytomegalovirus (CMV) downstream from the origin of replication. A number of unique restriction enzyme cleavage sites for insertion of antisense sequences are downstream of the promoter sequence. Located between the promoter and ribozyme cassette are the polyoma antisenseearly sequences. These sequences include polyoma nt 359-2908, spanning from about 230 base pairs (bp) downstream of the early TATA consensus sequence to a nucleotide 5 bp upstream of the early polyadenylation signal, AAUAAA.

Figure 1:
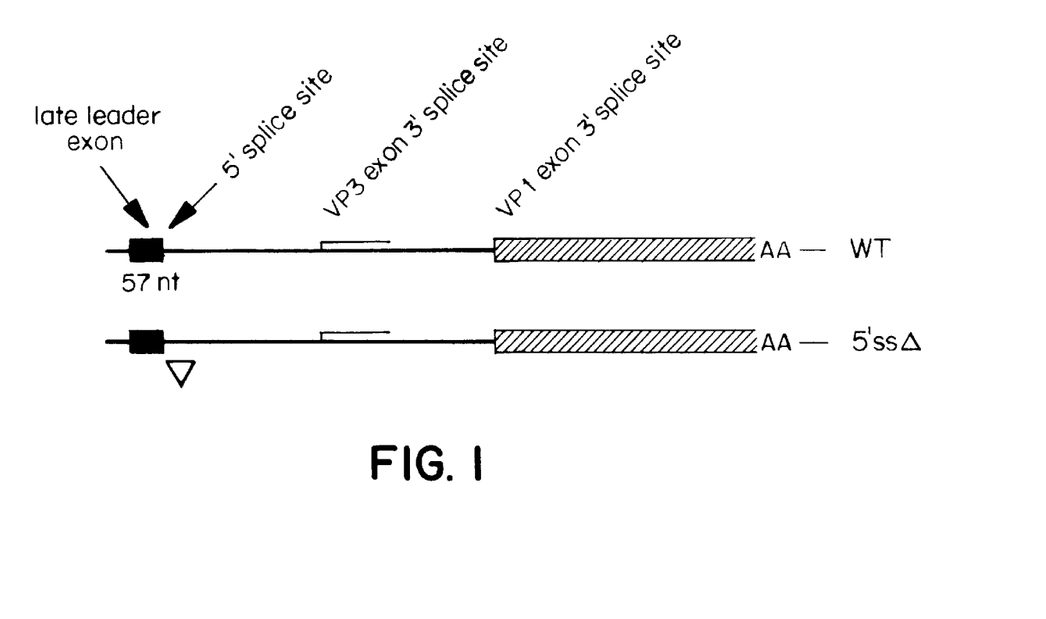
Figure 3:
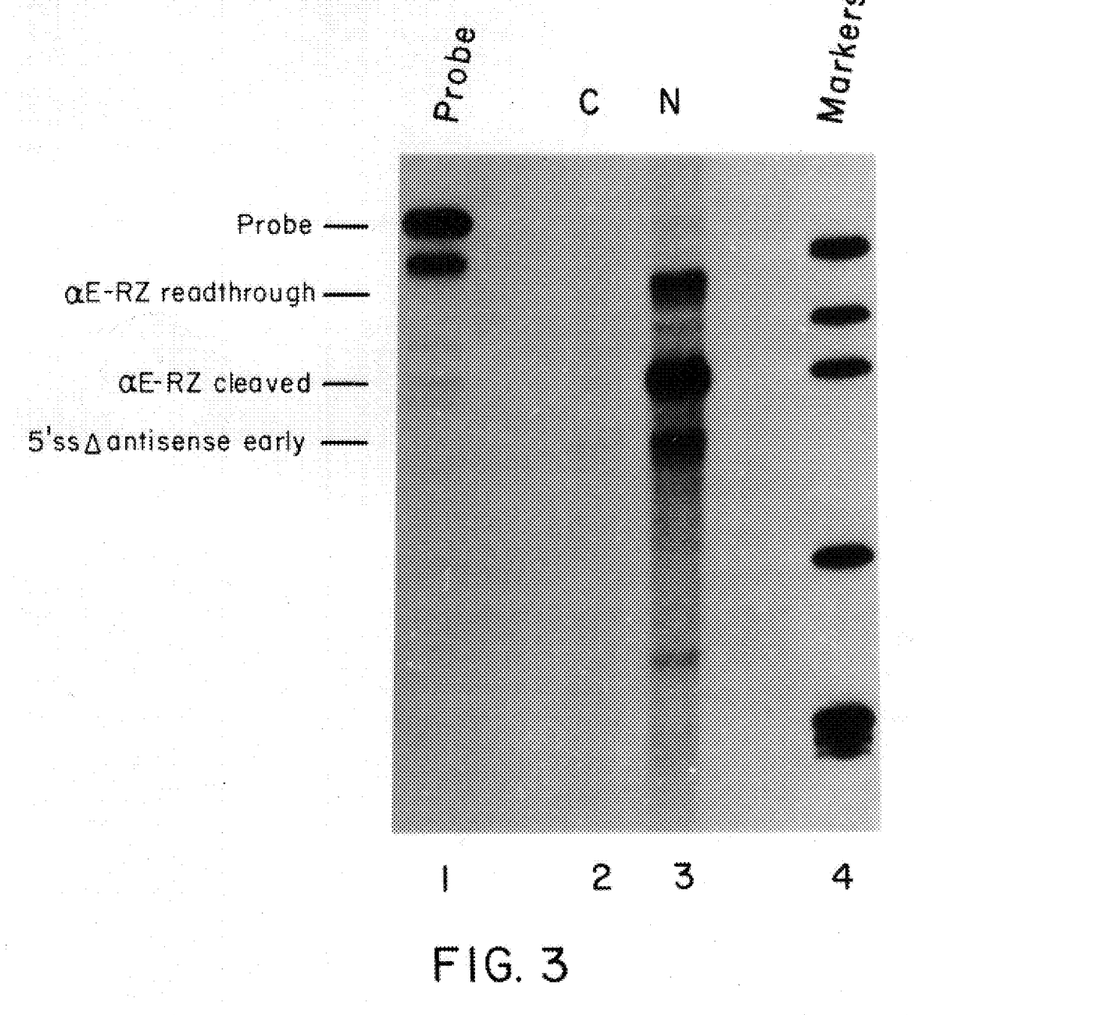
Figure 4A:
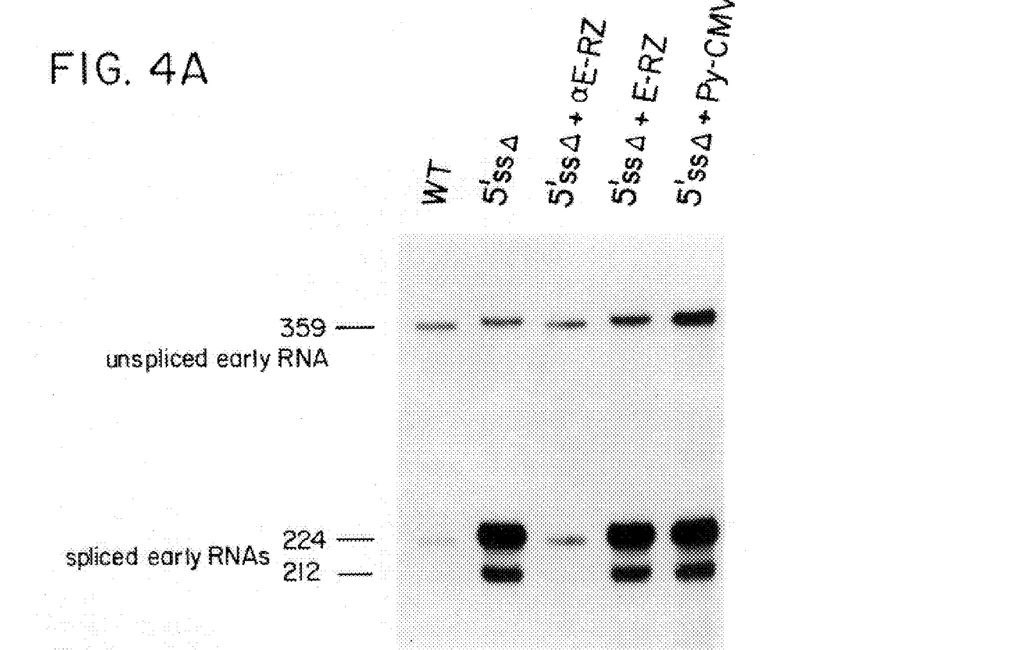
FIGS. 4A–4B show dose-dependent inhibition of early-strand RNA accumulation by nuclear antisense RNA in trans. A. Inhibition of early-strand RNAs by antisense RNA in trans. Lane 1: wild type transfection; lanes 2–5: the same amount of mutant 5'ssΔ was transfected by itself (lane 2), or co-transfected with a 9 fold molar excess of αE-RZ (lane 3), E-RZ (lane 4) and Py-CMV (lane 5), respectively. B. Dose-dependent effect of antisense RNA on polyoma early transcripts. The same amount of 5'ssΔ was co-transfected with nuclear antisense RNA expression vector αE-RZ at various molar ratios as indicated. The relative levels of early-strand RNAs are shown. Values have been corrected for probe length and U content. The numbers shown represent the average of two independent sets of experiments.
Figure 4B:
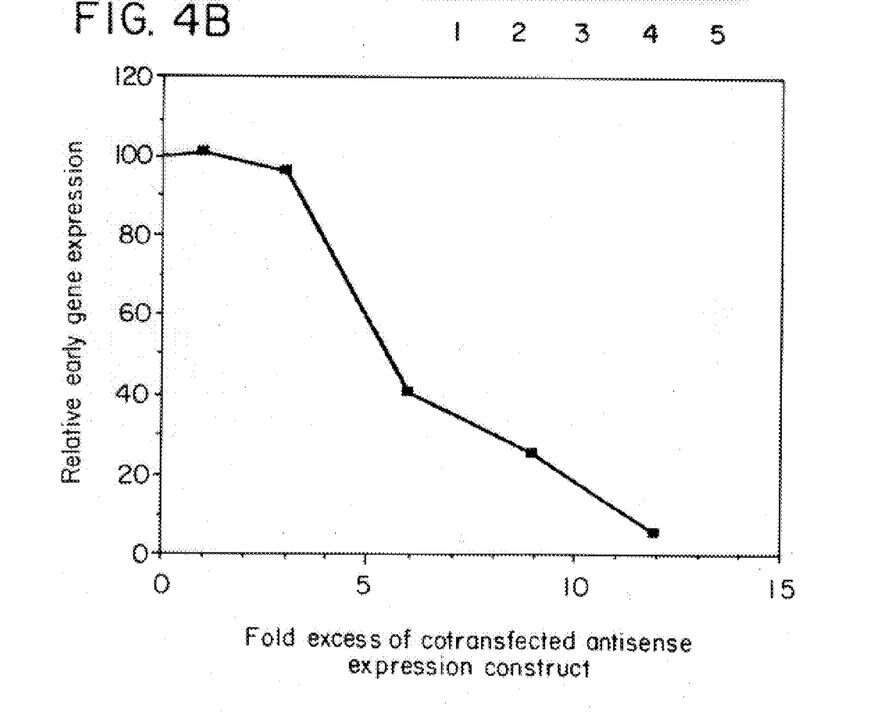

Mouse NIH 3T3 cells were co-transfected with construct αE-RZ and mutant 5'ssΔ. This polyoma virus mutant lacks 6 nt at the 5' splice site bordering the late leader, and overexpresses early-strand RNA by approximately 3 fold in comparison with wild type (FIG. 1). Thus, this mutant was used in place of wild type polyoma virus to allow more accurate determinations of antisense regulation. Nuclear and cytoplasmic RNA samples were isolated, and these samples were probed with an RNA probe that detects antisense early sequences from both constructs. The results (FIG. 3) showed that essentially all antisense RNA produced from construct αE-RZ remains in the nucleus, as does the RNA from the mutant 5'ssΔ. In further experiments a constant amount of construct 5'ssΔ was co-transfected into NIH 3T3 cells with increasing levels of αE-RZ, and early RNA levels from construct 5'ssΔ were measured using an RNAse protection assay as described in the Examples. These results (FIG. 4) confirm that while mutant 5'ssΔ over expresses nuclear early RNAs relative to wild type, when this construct is co-transfected with a nine-fold excess of construct αE-RZ early RNA expression was reduced to approximately the level of wild type expression. Control co-transfections using the same amounts of control constructs E-RZ, a promoterless version of αE-RZ and Py-CMV, the same as α-RZ but lacking polyoma early antisense regions (FIG. 2A) showed no decrease in early RNA levels from 5'ssΔ (FIG. 4A, lanes 4and 5). FIG. 4B shows the dose-response analysis. Increasing amounts of αE-RZ resulted in a striking diminution in 5'ssΔ early-strand RNA levels. DNA replication assays were performed to ensure that observations did not result from change in level of DNA replication.

To further illustrate the generality of the method, a vector using the Rous sarcoma virus promoter was used to drive expression of antisense RNA to the bacterial chloramphenicol acetyltransferase (CAT) gene in cotransfection experiments in mouse 3T3 cells. The assay shows that a six-fold excess of antisense-expressing plasmid leads to about a ten-fold reduction in CAT gene expression.

In another embodiment, specific sequences are incorporated into the nuclear antisense RNAs of the construct to increase their levels. Specifically, it is believed that a sequence containing part of a recognized RNA splicing signal will improve the stability of the nuclear RNA molecules when placed near their 5' ends.

In an alternate embodiment, the cis-ribozyme of construct αE-RZ is replaced with another ribozyme that is derived from the human hepatitis delta virus. It is reported that this ribozyme is far more efficient in vivo, compared to the ribozyme exemplified herein, and this may lead to higher levels of expressed nuclear antisense RNA.

Another embodiment of this invention incorporates sequences derived from the human Epstein Barr virus which will allow DNA replication. These sequences include the "oriP" sequence and the EBNA-1 gene; thus the vector will be able to replicate every time the cell replicates, and thereby be maintained in the cell over long periods of time.

In an alternate embodiment, the vector can be used to deliver not only antisense RNA but also antisense ribozymes that are capable of cleaving targeted RNA molecules in trans. There is growing literature on trans-ribozyme RNA cleavage, but again all systems use molecules that are targeted to the cytoplasm rather than the nucleus. (Steinecke, et al., *EMBO J.* 11:1525–1530 (1992)).

In another embodiment, the early region of the monkey virus SV40 (which infects all primate cells) can be removed and replaced with the nuclear antisense expression cassette as described above. The SV40 late region can be left intact, and these molecules will be introduced into monkey cells that express the SV40 early proteins (COS cells), thereby allowing efficient replication of these molecules. The result of this transfection will be the production of non-viable progeny virus particles, which are capable of expressing antisense RNA. Virus can be recovered from transfected cultures of COS cells and used to infect progeny cells. These viruses can enter cells and express the antisense genes, but are incapable of replication and cannot express SV40 late-region genes. This will allow delivery of nuclear antisense molecules efficiently and simultaneously to a large number of cells, including human cells.

This invention can be formulated in a preparation comprising the construct and a physiologically acceptable carrier. The preparation of this invention can be administered orally (e.g., capsular, tablet or liquid formulation), parenterally (e.g., intramuscularly, intravenously, subcutaneously) or topically in dosage formulations containing physiologically acceptable vehicle and optional adjuvants and preservatives. Suitable physiologically acceptable vehicles include saline, sterile water, Ringer's solution and isotonic sodium chloride solutions. The specific dosage level of active ingredient will depend upon a number of factors, including biological activity of the particular preparation, age, body weight, sex, general health and clinical diagnosis.

This invention also has utility as a research tool, in that it allows the regulation and inhibition of expression of various genes. This ability to selectively inhibit gene expression has potential for the study of virtually any gene expressed in eukaryotic cells.

The following Examples are offered for the purpose of illustrating the present invention and are not to be construed to limit the scope of this invention.

EXEMPLIFICATION

The teachings of all references are incorporated herein by reference.

Example 1

Materials

All restriction enzymes, T4 DNA ligase, large fragment of DNA polymerase (Klenow enzyme) and T4 polynucleotide kinase were from New England Biolabs and were used as suggested by the manufacturer. Calf intestine alkaline phosphatase was from Boehringer Mannheim. An RNAse T1/T2 mixture was made and used as described (Lichtler et al., *Biotechniques* 12:231–232 (1990)). T3 and T7 RNA polymerases and RNAse free RQ1 DNAse were from Promega Corp. The Random Primers DNA Labeling System was from Bethesda Research Laboratories. [α-$^{32}$P]UTP and [α-$^{32}$P] dATP were from Amersham Corp. GeneScreen Plus hybridization transfer membranes were from NEN Products of Dupont and used as recommended. Oligonucleotides were synthesized using a Milligen/Biosearch cyclone DNA synthesizer and phosphoramidite chemistry.

Example 2

Plasmid Constructions

Standard DNA cloning techniques (Maniatis et al., *Cold Spring Harbor Laboratory Manual,* Cold Spring Harbor Laboratory, Cold Spring Harbor, N.Y., 1982) were used in the construction of all plasmids. Polyoma virus strain 59RA (Feunteun et al., *Proc. Natl. Acad. Sci. USA* 68:283–288 (1986)) was cloned into the EcoRI site of a modified pUC18 vector and was used as the wild type virus. Constructs 5'ssΔ and ALM were described previously (Adami and Carmichael, Ibid., Barrett et al., Ibid.). Plasmid BS-RZ was generated by inserting annealed oligonucleotides comprising the histone stem loop-ribozyme oligonucleotide shown in FIG. 2B into pBlueScript SKII opened with EcoRV and SmaI. To create E-RZ, nt 359-2908 of 59RA (using the numbering system of Soeda et al., *Nature* 283:445–453 (1980)) were inserted at the BamHI site of BS-RZ that had been filled in with Klenow enzyme. The CMV promoter excised from pcDNA I/Amp (Invitrogen Corp.) with EcoRV (nt 3023) and DraI (nt 2276) was inserted at the filled-in BamHI site of polyoma strain 59RA to create Py-CMV.

Construct αE-RZ was created by inserting the Klenow-filled NarI-HindIII fragment of Py-CMV containing the polyoma replication origin and the CMV promoter into the SmaI site of E-RZ. Construct Ribo-Ava was created by inserting the AvaI fragment spanning the cleavage site of the ribozyme of αE-RZ. The clones used to generate RNA probes Ea and L4 were described previously (Liu and Carmichael, Ibid.).

Example 3

Cell Culture, Transfection, Infection and RNA Isolation

Mouse NIH 3T3 and 3T6 cells were maintained and propagated as described by Cahill et al. (J. Virol. 64:992–1001 (1990)). Cells were seeded at a density of $1 \times 10^6$/150-mm plate 24 hours prior to transfections or infection. For transfection, the polyoma virus constructs (wild type, ALM and 5'ssΔ) were released from the recombinant plasmids with proper restriction enzymes (EcoRI or BamHI) and recircularized with T4 DNA ligase under diluted conditions (<10 μg DNA/ml). Transfection followed a standard BES procedure (Chen and Okayama, Mol. Cell. Biol. 7:2745–2752 (1987)). Construct αE-RZ was cotransfected into NIH 3T3 cells along with mutant 5'ssΔ at various molar ratios as indicated in FIGS. 3 and 4. Infection of NIH 3T6 cells with strain 59RA was as described by Adami and Carmichael (Nucleic Acids Res. 15:2593–2610 (1987)). A single step method using guanidinium thiocyanate (Xie and Rothblum, BioTechniques 11:325–327 (1991)) was used to isolate total RNA. In brief, cells were lysed with a solution containing 4M guanidinium thiocyanate, 25 mM sodium citrate pH 7.0, 0.5% Sarcosyl and 0.1 M mercaptoethanol. The lysate was combined with an equal volume of water-saturated phenol and one fifth volume of chloroform and then allowed to sit on ice for 15 minutes. After centrifugation the aqueous phase was removed and precipitated with an equal volume of isopropanol. Nuclear and cytoplasmic RNAs were isolated as described by Hyde-DeRuyscher and Carmichael (J. Virol. 64:5823–5832 (1990)). Nuclear and cytoplasmic RNA samples isolated 48 hours post transfection were analyzed by an RNAse protection assay with the RNA probe Ribo-Ava (see FIG. 2A). To minimize DNA contamination, the RNA samples were extracted twice with acidic phenol as described in Liu and Carmichael, Ibid.

Example 4

RNAse Protection Assays

The clones used to generate RNA probes were linearized with appropriate restriction enzymes. Following in vitro transcription using T3 or T7 RNA polymerase and [α-$^{32}$p] UTP, DNA templates were removed by RQ1 DNAse digestion in combination with acid-phenol extraction. The lengths of protected probes were 421 nt for unprocessed antisense transcripts containing cis-ribozyme, 337 nt for transcripts cleaved by the cis-ribozyme, and 305 nt for early antisense transcripts deriving from mutant 5'SSΔ. The labeled RNA probes were hybridized in excess to RNA samples at 57-600C overnight (Adami et al., J. Virol. 63:85–93 (1989)). The resulting hybrids were then digested with T1/T2 mixture (Lichtler et al., Ibid.) at 37° C. for 2 hours. The reactions were stopped by adding 0.8 volumes of GTCN solution described above containing 20 μg glycogen as carrier. Undigested RNA fragments were then precipitated with an equal volume of isopropanol at −70° C. Samples recovered by centrifugation were resolved on 6% denaturing polyacrylamide sequencing gels. Quantitation of band intensities was performed using a Betagen Betascope Blot Analyzer. Control experiments using variable amounts of RNA probes confirmed that all RNAse protection experiments were carried out in probe excess.

Example 5

DNA Replication Assays

Episomal DNA was isolated as described by Hirt (J. Mol. Biol. 26:365–369 (1967)) and digested with an excess of DpnI, EcoRI and BamHI. Southern blot analysis of DNA replication was as described (Cahill et al., Ibid.) with a probe made by random priming the AvaI fragments (nt 657–1016) of 59RA.

Equivalents

Those skilled in the art will recognize, or be able to ascertain, using no more than routine experimentation, many equivalents to the specific embodiments of the invention described herein. Such equivalents are intended to be encompassed by the following claims:

We claim:
1. An isolated mammalian cell containing a DNA construct comprising:

a. a transcriptional promoter which provides efficient expression of an operably linked DNA segment such that inhibition of expression of a gene can be achieved with a 5-fold excess of antisense over sense RNA;

b. a DNA segment operably linked to said transcriptional promoter; and c. sequences encoding a cis-ribozyme operably linked to said DNA segment, such that expression of the DNA segment produces a ribonucleotide sequence which is complementary to a ribonucleotide sequence transcribed from a gene, and said expressed ribonucleotide sequence is accumulated in the cell nucleus and inhibits the expression of said gene.

2. An isolated mammalian cell containing a vector having incorporated therein a DNA construct comprising:

a. a transcriptional promoter which provides efficient expression of an operably linked DNA segment such that inhibition of expression of a gene can be achieved with a 5-fold excess of antisense over sense RNA;

b. a DNA segment operably linked to said transcriptional promoter; and c. sequences encoding a cis-ribozyme operably linked to said DNA segment, such that expression of the DNA segment produces a ribonucleotide sequence which is complementary to a ribonucleotide sequence transcribed from a gene, and said expressed ribonucleotide sequence is accumulated in the cell nucleus and inhibits the expression of said gene.

3. A method of inhibiting the expression of a gene in a mammalian cell comprising introducing into a mammalian cell a DNA construct comprising:

a. a transcriptional promoter which provides efficient expression of an operably linked DNA segment such that inhibition of expression of a gene can be achieved with a 5-fold excess of antisense over sense RNA;

b. a DNA segment operably linked to said transcriptional promoter; and c. sequences encoding a cis-ribozyme operably linked to said DNA segment, such that expression of the DNA segment produces a ribonucleotide sequence which is complementary to a ribonucleotide sequence transcribed from a gene, and said expressed ribonucleotide sequence is accumulated in the cell nucleus and inhibits the expression of said gene.

4. A method of inhibiting the expression of a gene in a mammalian cell, comprising the steps of:

a. introducing into a mammalian cell a DNA construct comprising:

i. a transcriptional promoter which provides efficient expression of an operably linked DNA segment such that inhibition of expression of a gene can be achieved with a 5-fold excess of antisense over sense RNA;

ii. a DNA segment operably linked to said transcriptional promoter; and iii. sequences encoding a cis-ribozyme operably linked to said DNA segment, such that expression of the DNA segment produces a ribonucleotide sequence which is complementary to a ribonucleotide sequence transcribed from a gene, and said expressed ribonucleotide sequence is accumulated in the cell nucleus and inhibits the expression of said gene, whereby a transformed cell is obtained; and b. expressing the DNA segment to thereby inhibit the expression of said gene.

5. A DNA construct comprising:

a. a human cytomegalovirus promoter or Rous sarcoma virus promoter;

b. a DNA segment operably linked to said promoter; and c. sequences encoding a cis-ribozyme operably linked to said DNA segment, such that expression of the DNA segment produces a ribonucleotide sequence which is complementary to a ribonucleotide sequence transcribed from a gene, and said expressed ribonucleotide sequence is accumulated in the cell nucleus and inhibits the expression of said gene.

6. A cell containing the construct of claim 5.

7. A vector having incorporated therein the construct of claim 5.

8. A vector according to claim 7 wherein said vector is a plasmid.

9. A composition comprising the construct of claim 5 and a physiologically acceptable vehicle.

10. A composition comprising the vector of claim 7 and a physiologically acceptable vehicle.

11. A composition comprising the vector of claim 8 and a physiologically acceptable vehicle.

12. A method of inhibiting the expression of a gene in a cell, comprising introducing into a cell a DNA construct comprising:

a. a human cytomegalovirus promoter or Rous sarcoma virus promoter;

b. a DNA segment operably linked to said promoter; and c. sequences encoding a cis-ribozyme operably liked to said DNA segment, such that expression of the DNA segment produces a ribonucleotide sequence which is complementary to a ribonucleotide sequence transcribed from a gene, and said expressed ribonucleotide sequence is accumulated in the cell nucleus and inhibits the expression of said gene.

13. A method of inhibiting the expression of a gene in a cell, comprising the steps of:

a. introducing into said cell a DNA construct comprising:

i. a human cytomegalovirus promoter or a Rous sarcoma virus promoter;

ii. a DNA segment operably linked to said transcriptional promoter; and iii. sequences encoding a cis-ribozyme operably linked to said DNA segment, such that expression of the DNA segment produces a ribonucleotide sequence which is complementary to a ribonucleotide sequence transcribed from a gene, and said expressed ribonucleotide sequence is accumulated in the cell nucleus and regulates the expression of said gene, whereby a transformed cell is obtained; and b. expressing the DNA segment to thereby inhibit the expression of said gene.

* * * * *